United States Patent
Evangelisti et al.

(10) Patent No.: US 7,087,688 B2
(45) Date of Patent: Aug. 8, 2006

(54) MAGNESIUM DICHLORIDE-ETHANOL ADDUCT AND CATALYST COMPONENTS OBTAINED THEREFROM

(75) Inventors: Daniele Evangelisti, Ferrara (IT); Gianni Collina, Ferrara (IT); Ofelia Fusco, Ferrara (IT); Mario Sacchetti, Ferrara (IT)

(73) Assignee: Basell Poliolefine Italia S.p.A., Milan (IT)

( * ) Notice: Subject to any disclaimer, the term of this patent is extended or adjusted under 35 U.S.C. 154(b) by 0 days.

(21) Appl. No.: 10/495,940

(22) PCT Filed: Aug. 21, 2003

(86) PCT No.: PCT/EP03/09282

§ 371 (c)(1),
(2), (4) Date: May 17, 2004

(87) PCT Pub. No.: WO2004/026920

PCT Pub. Date: Apr. 1, 2004

(65) Prior Publication Data

US 2004/0266610 A1 Dec. 30, 2004

Related U.S. Application Data

(60) Provisional application No. 60/413,690, filed on Sep. 26, 2002.

(30) Foreign Application Priority Data

Sep. 17, 2002 (EP) .................................. 02078875

(51) Int. Cl.
*C08F 4/42* (2006.01)

(52) U.S. Cl. ................... 526/123.1; 526/348; 526/352; 526/124.3; 502/103; 502/115; 502/125

(58) Field of Classification Search ................ 526/348, 526/352, 123.1, 124.3; 502/103, 115, 125
See application file for complete search history.

(56) References Cited

U.S. PATENT DOCUMENTS

| 4,399,054 A | * | 8/1983 | Ferraris et al. | ............. 502/125 |
| 6,071,846 A | * | 6/2000 | Kitajima et al. | ............. 502/125 |
| 6,437,061 B1 | | 8/2002 | Sacchetti et al. | ........ 526/124.2 |

FOREIGN PATENT DOCUMENTS

| EP | 0395083 | 10/1990 |
| EP | 0700936 | 3/1996 |
| WO | 9844009 | 10/1998 |
| WO | WO 98/44009 | * 10/1998 |

* cited by examiner

*Primary Examiner*—Ling-Sui Choi
(74) *Attorney, Agent, or Firm*—Jarrod N. Raphael; William R. Reid

(57) ABSTRACT

A $MgCl_2 \cdot mEtOH \cdot nH_2O$ adducts, where $3.4 < m \leq 4.4$, $0 \leq n \leq 0.7$, characterized by an X-ray diffraction spectrum, taken under the condition set forth above, in which, in the range of $2\theta$ diffraction angles between 5° and 10°, at least two diffraction lines are present at diffraction angles $2\theta$ of $9.3 \pm 0.2°$, and $9.9 \pm 0.2°$, the most intense diffraction lines being the one at $2\theta$ of $9.3 \pm 0.2°$, the intensity of the other diffraction line being less than 0.4 times the intensity of the most intense diffraction line. Catalyst components obtained from the adducts of the present invention are capable to give catalysts for the polymerization of olefins characterized by enhanced activity and/or porosity with respect to the catalysts prepared from the adducts of the prior art.

26 Claims, No Drawings

MAGNESIUM DICHLORIDE-ETHANOL ADDUCT AND CATALYST COMPONENTS OBTAINED THEREFROM

This application is the U.S. national phase of International Application PCT/EP2003/009282, filed Aug. 21, 2003.

The present invention relates to magnesium dichloride/ethanol adducts which are characterized by particular chemical and physical properties. The adducts of the present invention are particularly useful as precursors of catalyst components for the polymerization of olefins.

$MgCl_2$·alcohol adducts and their use in the preparation of catalyst components for the polymerization of olefins are well known in the art.

Catalyst components for the polymerization of olefins, obtained by reacting $MgCl_2$·nEtOH adducts with halogenated transition metal compounds, are described in U.S. Pat. No. 4,399,054. The adducts are prepared by emulsifying the molten adduct in an immiscible dispersing medium and quenching the emulsion in a cooling fluid to collect the adduct in the form of spherical particles. The number of moles of alcohol per mole of $MgCl_2$ is generally 3. In order to render the catalyst suitable to produce non-fragile polymer particles, the alcohol content of the adduct is lowered, before reaction with the titanium compound, to values in the range of 2–2.5 moles. As a downside, however, the catalyst activity becomes too low.

In WO98/44009 are disclosed $MgCl_2$·alcohol adducts having improved characteristics and characterized by a particular X-ray diffraction spectrum, in which, in the range of 2θ diffraction angles between 5° and 15°, the three main diffraction lines are present at diffraction angles 2θ of 8.8±0.2°, 9.4±0.2° and 9.8±0.2°, the most intense diffraction lines being the one at 2θ=8.8±0.2°, the intensity of the other two diffraction lines being at least 0.2 times the intensity of the most intense diffraction line. Said adducts can be of formula $MgCl_2$·mEtOH·nH$_2$O where m is between 2.2 and 3.8 and n is between 0.01 and 0.6. The catalyst components obtained from these adducts have an increased activity over those obtained from the adducts of U.S. Pat. No. 4,399,054. Also in this case the dealcoholation of the adducts before the reaction with the titanium compound (example 6) increases the porosity of the final catalyst but makes its activity much lower.

EP-A-700936 describes a process for producing a solid catalyst components for the polymerization of olefins which comprises the (A) the preparation of a $MgCl_2$·4EtOH solid adducts by means of spray-cooling a $MgCl_2$ and ethanol mixture; (B) partly removing the alcohol from the above-obtained solid adduct to obtain an adduct containing from 0.4 to 2.8 mol of alcohol per mol of $MgCl_2$. FIG. 2 of the said European Patent Application shows a typical X-ray diffraction spectrum of the adducts prepared in (A). The highest peak occurs at 2θ=8.8°; two less intense peaks occur at 2θ=9.5 to 10° and 2θ=13°, respectively. The adduct obtained in (B) is characterized by an X-ray diffraction spectrum in which a novel peak does not occur at a diffraction angles 2θ=7 to 8° as compared with the diffraction spectrum of the adduct obtained in (A), or even if it occurs, the intensity of the novel peak is 2.0 times or less the intensity of the highest peak present at the diffraction angles 2θ=8.5 to 9° of the diffraction spectrum of the adduct obtained in (B). FIG. 3 shows a typical X-ray diffraction spectrum of the adducts prepared in (B) and thus containing about 1.7 moles of ethanol. The highest peak occurs at 2θ=8.8°; other peaks occur at 2θ=6.0 to 6.5°, 2θ=9.5 to 10° and 2θ=11 to 11.5°. The applicant has now found new $MgCl_2$·mEtOH adducts having specific chemical and physical properties. The adducts of the present invention can be used to prepare catalyst components for the polymerization of olefins by reacting them with transition metal compounds. Catalyst components directly obtained from the adducts of the present invention are capable to give catalysts for the polymerization of olefins characterized by enhanced activity with respect to the catalyst of the prior art derived from non-dealcoholated adduct. An additional advantage is obtainable by the dealcoholation of the adducts which allows the preparation of catalysts with a higher porosity with respect to the prior art. Therefore, with the adducts of the invention it is possible to modulate the properties of the final catalyst in order to obtain, in comparison with the catalyst of the prior art, either a higher porosity and same activity or a higher activity with the same porosity level.

The present invention therefore relates to $MgCl_2$·mEtOH·nH$_2$O adducts were $3.4 < m \leq 4.4$, $0 \leq n \leq 0.7$, characterized by an X-ray diffraction spectrum, taken under the condition set forth below, in which, in the range of 2θ diffraction angles between 5° and 10°, at least two diffraction lines are present at diffraction angles 2θ of 9.3±0.2°, and 9.9±0.2°, the most intense diffraction lines being the one at 2θ of 9.3±0.2°, the intensity of the other diffraction line being less than 0.4 times the intensity of the most intense diffraction line.

Preferably, $3.8 < m \leq 4.2$, more preferably $3.9 < m \leq 4.1$ and $0 \leq n \leq 0.4$. Preferably the intensity of the peak at diffraction angles 2θ of 9.9±0.2° is less than 0.3 times the intensity of the most intense diffraction line. Preferably an additional diffraction line at diffraction angles 2θ of 8.1±0.2° having an intensity of less than 0.7 times the intensity of the diffraction line at diffraction angles 2θ of and 9.9±0.2° is present. Moreover, in some instances an additional diffraction line at diffraction angles 2θ of and 9.1±0.2° is present. This latter line has an intensity of from 0.6 to 0.9 times, preferably from 0.6 to 0.8, the intensity of the most intense diffraction line in the range of 2θ diffraction angles between 5° and 10°.

Particularly interesting are the adducts of the invention showing, in the DSC profile taken under the conditions set forth below, only one melting peak (Tm) in the range 90–105° C. g having an associated fusion enthalpy generally lower than 125 J/g and preferably lower than 110 J/g. If additional peaks in the region below 80° C. are present, the fusion enthalpy associated to them is lower than 30% of the total fusion enthalpy, preferably lower than 20 and more preferably lower than 10%. The DSC analysis is carried out using the apparatus and the methodology described hereinafter.

One of the preferred methods for preparing the adducts of the present invention comprises dispersing the particles of magnesium dichloride in an inert liquid immiscible with and chemically inert to the molten adduct, heating the system at temperature equal to or higher than the melting temperature of $MgCl_2$·ethanol adduct and then adding the desired amount of alcohol in vapour phase. The temperature is kept at values such that the adduct is completely melted. The molten adduct is then emulsified in a liquid medium which is immiscible with and chemically inert to it and then quenched by contacting the adduct with an inert cooling liquid, thereby obtaining the solidification of the adduct.

The liquid in which the $MgCl_2$ is dispersed can be any liquid immiscible with and chemically inert to the molten adduct. For example, aliphatic, aromatic or cycloaliphatic hydrocarbons can be used as well as silicone oils. Aliphatic hydrocarbons such as vaseline oil are particularly preferred. After the $MgCl_2$ particles are dispersed in the inert liquid, the mixture is heated at temperatures preferably higher than 95° C. and more preferably in the range 100–130° C. Conveniently, the vaporized alcohol is added at a temperature equal to or lower than the temperature of the mixture.

According to another method, the adducts of the invention are prepared by contacting MgCl$_2$ and alcohol in the absence of the inert liquid dispersant, heating the system at the melting temperature of MgCl$_2$-alcohol adduct or above, and maintaining said conditions so as to obtain a completely melted adduct. In particular, the adduct is preferably kept at a temperature equal to or higher than its melting temperature, under stirring conditions, for a time period equal to or greater than 2 hours, preferably from 2 to 15 hours, more preferably from 5 to 10 hours. Said molten adduct is then emulsified in a liquid medium which is immiscible with and chemically inert to it and finally quenched by contacting the adduct with an inert cooling liquid thereby obtaining the solidification of the adduct. It is also preferable, before recovering the solid particles, to leave them in the cooling liquid at a temperature ranging from –10 to 25° C. for a time ranging from 1 to 24 hours. Particularly in this method the solidification of the adduct in spherical particles can be obtained by spraying the MgCl$_2$-alcohol adduct, not emulsified, in an environment having a temperature so low as to cause rapid solidification of the particles.

All these methods provide solid adducts having a substantially spherical morphology and average diameter comprised between 5 and 150 μm which are very suitable in the preparation of spherical catalyst components for the polymerization of olefins and in particular for the gas-phase polymerization process. With the term substantial spherical morphology are meant those particles having a ratio between the greater and smaller axis equal to or lower than 1.5 and preferably lower than 1.3.

In order to not to exceed the maximum value of n contemplated by the above formula a particular attention should be paid to the water content of the reactants. Both MgCl$_2$ and EtOH are in fact highly hygroscopic and tend to incorporate water in their structure. As a result, if the water content of the reactants is relatively high, the final MgCl$_2$-EtOH adducts may contain a too high water content even if water has not been added as a separate component. Means for controlling or lowering the water content in solids or fluids are well known in the art. The water content in MgCl$_2$ can be for example lowered by drying it in an oven at high temperatures or by reacting it with a compound which is reactive towards water. As an example, a stream of HCl can be used to remove water from MgCl$_2$. Water from the fluids can be removed by various techniques such as distillation or by allowing the fluids to become in contact with substances capable to subtract water such as molecular sieves. Once this precautions have been taken, the reaction between the magnesium chloride and ethanol to produce the adducts of the invention can be carried out according to various methods.

Upon reaction with transition metal compounds, the adducts of the invention form suitable catalyst components for the polymerization of olefins.

The adducts can be reacted as such with the transition metal compound or, in alternative, they can be subject to a preliminary step of dealcoholation.

Among transition metal compounds particularly preferred are titanium compounds of formula Ti(OR)$_n$X$_{y-n}$ in which n is comprised between 0 and y; y is the valence of titanium; X is halogen and R is an hydrocarbon radical, preferably alkyl, radical having 1–10 carbon atoms or a COR' group wherein R' is an alkyl radical having 1–8 carbon atoms. Among them, particularly preferred are titanium compounds having at least one Ti-halogen bond such as titanium tetrahalides or halogenalcoholates. Preferred specific titanium compounds are TiCl$_3$, TiCl$_4$, Ti(OBu)$_4$, Ti(OBu)Cl$_3$, Ti(OBu)$_2$Cl$_2$, Ti(OBu)$_3$Cl. Preferably, the reaction is carried out by suspending the adduct in cold TiCl$_4$ (generally 0° C.); then the so obtained mixture is heated up to 80–130° C. and kept at this temperature for 0.5–2 hours. After that the excess of TiCl$_4$ is removed and the solid component is recovered. The treatment with TiCl$_4$ can be carried out one or more times.

The reaction between transition metal compound and the adduct can also be carried out in the presence of an electron donor compound (internal donor) in particular when the preparation of a stereospecific catalyst for the polymerization of olefins is to be prepared. Said electron donor compound can be selected from esters, ethers, amines, silanes and ketones. In particular, the alkyl and aryl esters of mono or polycarboxylic acids such as for example esters of benzoic, phthalic, malonic and succinic acid are preferred. Specific examples of such esters are n-butylphthalate, diisobutylphthalate, di-n-octylphthalate, diethyl 2,2-diisopropylsuccinate, diethyl 2,2-dicyclohexyl-succinate, ethyl-benzoate and p-ethoxy ethyl-benzoate. Moreover, can be advantageously used also the 1,3 diethers of the formula:

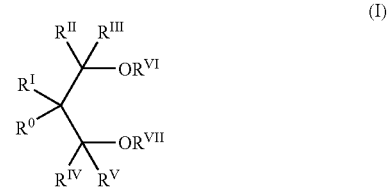

(I)

wherein R$^O$, R$^I$, R$^{II}$, R$^{III}$, R$^{IV}$ and R$^V$ equal or different to each other, are hydrogen or hydrocarbon radicals having from 1 to 18 carbon atoms, and R$^{VI}$ and R$^{VII}$, equal or different from each other, have the same meaning of R—R$^V$ except that they cannot be hydrogen; one or more of the R—R$^{VII}$ groups can be linked to form a cycle. The 1,3-diethers in which R$^{VI}$ and R$^{VII}$ are selected from C$_1$-C$_4$ alkyl radicals are particularly preferred.

The electron donor compound is generally present in molar ratio with respect to the magnesium comprised between 1:4 and 1:20.

Preferably, the particles of the solid catalyst components replicate those of the solid adducts illustrated above, thus showing a substantially spherical morphology and an average diameter comprised between 5 and 150 μm.

As mentioned before the reaction with the transition metal compound, the adducts of the present invention can also be subjected to a dealcoholation treatment aimed at lowering the alcohol content and increasing the porosity of the adduct itself. The dealcoholation can be carried out according to known methodologies such as those described in EP-A-395083. Depending on the extent of the dealocholation treatment, partially dealcoholated adducts can be obtained having an alcohol content generally ranging from 0.1 to 3 moles of alcohol per mole of MgCl$_2$ and a porosity (determined with Hg method described below)) ranging from 0.05 to 2 cc/g. Among this class particularly interesting are the dealcoholated adducts containing from 1 to 3 moles of alcohol and porosity in the range of 0.15 to 1.5 cc/g. After the dealcoholation treatment the adducts are reacted with the transition metal compound, according to the techniques described above, in order to obtain the solid catalyst components. As mentioned before the solid catalyst components according to the present invention show a porosity (determined with Hg method) higher than 0.2 cm$^3$/g preferably between 0.25 and 2 cm$^3$/g.

Surprisingly, the catalyst components comprising the reaction product of a transition metal compound with a MgCl$_2$-alcohol adduct which is in turn obtained by partially dealcoholating the adducts of the invention, show improved properties, particularly in terms of activity and porosity, with respect to the catalyst components prepared from the dealcoholated adducts of the prior art. Particularly interesting are the catalyst obtained by reacting the transition metal compound with dealcoholated adducts containing from 1 to 3 moles of alcohol. The so obtained catalysts have an higher porosity with respect to the catalyst obtained by the adducts of the prior art, such as those of WO98/44009, having the corresponding alcohol content. On the other hand, for the same porosity, the catalyst of the invention are more active than those of the prior art.

The catalyst components of the invention form catalysts for the polymerization of alpha-olefins CH$_2$=CHR$^4$, wherein R$^4$ is hydrogen or a hydrocarbon radical having 1–12 carbon atoms, by reaction with Al-alkyl compounds. The alkyl-Al compound is preferably chosen among the trialkyl aluminum compounds such as for example triethylaluminum, triisobutylaluminum, tri-n-butylaluminum, tri-n-hexylaluminum, tri-n-octylaluminum. It is also possible to use alkylaluminum halides, alkylaluminum hydrides or alkylaluminum sequichlorides such as AlEt$_2$Cl and Al$_2$Et$_3$Cl$_3$ optionally in mixture with said trialkyl aluminum compounds.

The Al/Ti ratio is higher than 1 and is generally comprised between 20 and 800. In the case of the stereoregular polymerization of α-olefins such as for example propylene and 1-butene, an electron donor compound (external donor) which can be the same or different from the compound used as internal donor can be used in the preparation of the catalysts disclosed above. In case the internal donor is an ester of a polycarboxylic acid, in particular a phthalate, the external donor is preferably selected from the silane compounds containing at least a Si—OR link, having the formula $R_a^1 R_b^2 Si(OR^3)_c$, where a and b are integer from 0 to 2, c is an integer from 1 to 3 and the sum (a+b+c) is 4; R$^1$, R$^2$, and R$^3$, are alkyl, cycloalkyl or aryl radicals with 1–18 carbon atoms. Particularly preferred are the silicon compounds in which a is 1, b is 1, c is 2, at least one of R$^1$ and R$^2$ is selected from branched alkyl, cycloalkyl or aryl groups with 3–10 carbon atoms and R$^3$ is a C$_1$-C$_{10}$ alkyl group, in particular methyl. Examples of such preferred silicon compounds are methylcyclohexyldimethoxysilane, diphenyldimethoxysilane, methyl-t-butyldimethoxysilane, dicyclopentyldimethoxysilane. Moreover, are also preferred the silicon compounds in which a is 0, c is 3, R$^2$ is a branched alkyl or cycloalkyl group and R$^3$ is methyl. Examples of such preferred silicon compounds are cyclohexyltrimethoxysilane, t-butyltrimethoxysilane and thexyltrimethoxysilane.

Also the 1,3 diethers having the previously described formula can be used as external donor. However, in the case 1,3-diethers are used as internal donors, the use of an external donor can be avoided, as the stereospecificity of the catalyst is already sufficiently high.

As previously indicated the components of the invention and catalysts obtained therefrom find applications in the processes for the (co)polymerization of olefins of formula CH$_2$=CHR in which R is hydrogen or a hydrocarbon radical having 1–12 carbon atoms.

The catalysts of the invention can be used in any of the olefin polymerization processes known in the art. They can be used for example in slurry polymerization using as diluent an inert hydrocarbon solvent or bulk polymerization using the liquid monomer (for example propylene) as a reaction medium. Moreover, they can also be used in the polymerization process carried out in gas-phase operating in one or more fluidized or mechanically agitated bed reactors.

The polymerization is generally carried out at temperature of from 20 to 120° C., preferably of from 40 to 80° C. When the polymerization is carried out in gas-phase the operating pressure is generally between 0.1 and 10 MPa, preferably between 1 and 5 MPa. In the bulk polymerization the operating pressure is generally between 1 and 6 MPa preferably between 1.5 and 4 MPa.

The catalysts of the invention are very useful for preparing a broad range of polyolefin products. Specific examples of the olefinic polymers which can be prepared are: high density ethylene polymers (HDPE, having a density higher than 0.940 g/cc), comprising ethylene homopolymers and copolymers of ethylene with alpha-olefins having 3–12 carbon atoms; linear low density polyethylenes (LLDPE, having a density lower than 0.940 g/cc) and very low density and ultra low density (VLDPE and ULDPE, having a density lower than 0.920 g/cc, to 0.880 g/cc) consisting of copolymers of ethylene with one or more alpha-olefins having from 3 to 12 carbon atoms, having a mole content of units derived from the ethylene higher than 80%; isotactic polypropylenes and crystalline copolymers of propylene and ethylene and/or other alpha-olefins having a content of units derived from propylene higher than 85% by weight; copolymers of propylene and 1-butene having a content of units derived from 1-butene comprised between 1 and 40% by weight; heterophasic copolymers comprising a crystalline polypropylene matrix and an amorphous phase comprising copolymers of propylene with ethylene and or other alpha-olefins.

The following examples are given to illustrate and not to limit the invention itself.

Characterization

The properties reported below have been determined according to the following methods:

X-ray diffraction spectra were carried out with a Philips PW 1710 instrument using the CuK$_\alpha$($\lambda$=1,5418Å) radiation and equipped with a monochromator, a 40 Kv tension generator, a 30 mA current generator, an automatic divergence slit and a receiving slit of 0.2 mm. The X-ray diffraction patterns were recorded in the range between 2θ=5° and 2θ=15° with a scanning rate of 0.02° 2θ/18 sec. The instrument was calibrated using the ASTM 27-1402 standard for Silicon. The samples to be analyzed were closed in a polyethylene bas of 50 μm thickness operating in a dry-box.

The DSC measurement were carried out with a Perkin Elmer instrument at a scanning rate of 5° C./min in the range 5–125° C. Aluminum capsules having a volume of 40 μl filled with the samples in a dry-box were used in order to avoid hydration of the samples.

Porosity and surface area with nitrogen: are determined according to the B.E.T. method (apparatus used SORPTOMATIC 1900 by Carlo Erba).

Porosity and Surface Area with Mercury:

The measure is carried out using a "Porosimeter 2000 series" by Carlo Erba.

The porosity is determined by absorption of mercury under pressure. For this determination use is made of a calibrated dilatometer (diameter 3 mm) CD$_3$ (Carlo Erba)

connected to a reservoir of mercury and to a high-vacuum pump (1–10⁻² mbar). A weighed amount of sample is placed in the dilatometer. The apparatus is then placed under high vacuum (<0.1 mm Hg) and is maintained in these conditions for 20 minutes. The dilatometer is then connected to the mercury reservoir and the mercury is allowed to flow slowly into it until it reaches the level marked on the dilatometer at a height of 10 cm. The valve that connects the dilatometer to the vacuum pump is closed and then the mercury pressure is gradually increased with nitrogen up to 140 kg/cm². Under the effect of the pressure, the mercury enters the pores and the level goes down according to the porosity of the material.

The porosity (cm³/g), due to pores up to 0.1 mm, the pore distribution curve, and the average pore size are directly calculated from the integral pore distribution curve which is function of the volume reduction of the mercury and applied pressure values (all these data are provided and elaborated by the porosimeter associated computer which is equipped with a "MILESTONE 200/2.04" program by C. Erba.

The DSC measurement were carried out with a METTLER DSC 30 instrument at a scanning rate of 5° C./min in the range 5–125° C. Aluminum capsules having a volume of 40 μl filled with the samples in a dry-box were used in order to avoid hydration of the samples.

EXAMPLES

General Procedure for the Preparation of the Catalyst Component

Into a 1 l steel reactor provided with stirrer, 800 cm³ of TiCl₄ at 0° C. were introduced; at room temperature and whilst stirring 16 g of the adduct were introduced together with an amount of diisobutylphthalate as internal donor so as to give a donor/Mg molar ratio of 10. The whole was heated to 100° C. over 90 minutes and these conditions were maintained over 120 minutes. The stirring was stopped and after 30 minutes the liquid phase was separated from the sedimented solid maintaining the temperature at 100° C. A further treatment of the solid was carried out adding 750 cm³ of TiCl₄ and heating the mixture at 120° C. over 10 min. and maintaining said conditions for 60 min under stirring conditions (500 rpm). The stirring was then discontinued and after 30 minutes the liquid phase was separated from the sedimented solid maintaining the temperature at 120° C. Thereafter, 3 washings with 500 cm³ of anhydrous hexane at 60° C. and 3 washings with 500 cm³ of anhydrous hexane at room temperature were carried out. The solid catalyst component obtained was then dried under vacuum in nitrogen environment at a temperature ranging from 40–45° C.

General Procedure for the Polymerization Test

A 4 liter steel autoclave equipped with a stirrer, pressure gauge, thermometer, catalyst feeding system, monomer feeding lines and thermostatting jacket, was used. The reactor was charged with 0.01 gr. of solid catalyst component 0,76 g of TEAL, 0.076 g of dicyclopentyldimetoxy silane, 3.2 l of propylene, and 1.5 l of hydrogen. The system was heated to 70° C. over 10 min. under stirring, and maintained under these conditions for 120 min. At the end of the polymerization, the polymer was recovered by removing any unreacted monomers and was dried under vacuum.

Example 1

In a vessel reactor equipped with a IKA RE 166 stirrer containing 181.64 g of anhydrous EtOH at −8° C. were introduced under stirring 93.26 gr. of MgCl₂ containing 0.3% water. Once the addition of MgCl₂ was completed, the temperature was raised up to 108° C. and kept at this value for 3 hours. After that, 1600 cm³ of OB55 vaseline oil were introduced and, while keeping the temperature at 108° C., the stirring was brought to 1500 rpm and kept at that value for two minutes. After that time the mixture was discharged into a vessel containing hexane which was kept under stirring and cooled so that the final temperature did not exceed 12° C. After 12 hours, the solid particles of the MgCl₂·EtOH adduct recovered were then washed with hexane and dried at 40° C. under vacuum. The compositional analysis showed that they contained 64% by weight of EtOH and 0.4% of water.

The X-ray spectrum of the adduct showed in the range of 2θ diffraction angles between 5° and 10° one main diffraction line present at diffraction angles 2θ of 9.34° (100), and a side peak around 9,87 (10); the number in brackets represents the intensity I/I$_o$ with respect to the most intense line.

The DSC profile showed a peak at 95.8° C. with an associated fusion enthalpy of 102.3 J/g. The adduct was then used, according to the general procedure, for preparing the catalyst component the properties of which are reported in Table 1. The catalyst was then tested according to the general polymerization procedure described above and gave the results reported in Table 2.

Example 2

In a vessel reactor equipped with a IKA RE 166 stirrer containing 181 g of anhydrous EtOH at −6.5° C. temperature were introduced under stirring 93.14 g of MgCl₂ containing 0.3% water. Once the addition of MgCl₂ was completed, the temperature was raised up to 108° C. and kept at this value for 3 hours. After that, 1600 cm³ of OB55 vaseline oil were introduced and, while keeping the temperature at 105.5° C., the stirring was brought to 1500 rpm and kept at that value for two minutes. After that time the mixture was discharged into a vessel containing hexane which was kept under stirring and cooled so that the final temperature did not exceed 12° C. After 12 hours, the solid particles of the MgCl₂·EtOH adduct recovered were then washed with hexane and dried at 40° C. under vacuum. The compositional analysis showed that they contained 64.4% by weight of EtOH and 0.4% of water.

The X-ray spectrum of the adduct showed in the range of 2θ diffraction angles between 5° and 10° four diffraction lines present at diffraction angles 2θ of 8.11 (10), 9.41 (100), 9.11 (76) and 9.9° (16); the number in brackets represents the intensity I/I$_o$ with respect to the most intense line.

The DSC profile showed a peak at 98° C., with an associated fusion enthalpy of 104.4 J/g. The adduct was then used, according to the general procedure, for preparing the catalyst component the properties of which are reported in Table 1. The catalyst was then tested according to the general polymerization procedure described above and gave the results reported in Table 2.

Example 3

An MgCl₂—EtOH adduct prepared according to the procedure of Example 1 was thermally dealcoholated under nitrogen flow until the content of EtOH reached 40% b.w,. The so dealcoholated adduct showed a porosity of 0.617 cm³/g. Then, said dealcoholated adduct was used to prepare, according to the general procedure, the catalyst component the properties of which are reported in table 1. The catalyst was then used in a polymerization test carried out according to the procedure described above. The results are reported in Table 2.

Comparison Example 1

In a vessel reactor equipped with a IKA RE 166 stirrer containing 139.16 g of anhydrous EtOH at room temperature were introduced under stirring 95.64 gr. of $MgCl_2$ containing 0.3% water. Once the addition of $MgCl_2$ was completed, the temperature was raised up to 125° C. and kept at this value for 3 hours. After that, 1600 cm³ of OB55 vaseline oil were introduced and, while keeping the temperature at 125° C., the stirring was brought to 1500 rpm and kept at that value for two minutes. After that time the mixture was discharged into a vessel containing hexane which was kept under stirring and cooled so that the final temperature did not exceed 12° C. After 12 hours, the solid particles of the $MgCl_2 \cdot EtOH$ adduct recovered were then washed with hexane and dried at 40° C. under vacuum. The compositional analysis showed that they contained 58.5% by weight of EtOH and 0.3% of water.

The adduct was then used, according to the general procedure, for preparing the catalyst component the properties of which are reported in Table 1. The catalyst was then tested according to the general polymerization procedure described above and gave the results reported in Table 2.

Comparison Example 2

An $MgCl_2$—EtOH adduct prepared according to the procedure of Example 1 was thermally dealcoholated under nitrogen flow until the content of EtOH reached 40% b.w,. The so dealcoholated adduct showed a porosity of 0.3 cm³/g.

TABLE 1

| Example | Ti % wt | Mg % wt | ID % wt | Porosity Cm³/g |
|---|---|---|---|---|
| 1 | 2.9 | 18.1 | 12.8 | n.d. |
| 2 | 3 | 18.5 | 12.5 | n.d |
| 3 | 2.6 | 17.9 | 6.7 | 0.821 |
| Comp. 1 | 3 | 14.5 | 19.4 | n.d. |
| Comp. 2 | 2.8 | 19.2 | 6 | 0.562 |

TABLE 2

| Example | Activity | I.I: | Poured bulk density |
|---|---|---|---|
| 1 | 75 | 97.6 | 0.435 |
| 2 | 72 | 97.5 | 0.42 |
| 3 | 21 | 96.5 | 0.32 |
| Comp. 1 | 58 | 97.7 | 0.445 |
| Comp. 2 | 17.5 | 96.5 | 0.325 |

The invention claimed is:

1. A $MgCl_2 \cdot mEtOH \cdot nH_2O$ adduct, wherein $3.4<m \leq 4.4$, $0<n \leq 0.7$, the adduct having an X-ray diffraction spectrum comprising at least one diffraction line at each diffraction angle 2θ of 9.3±0.2° and 9.9±0.2° with each diffraction angle being between 5° and 10°, the diffraction line at diffraction angle 2θ of 9.3±0.2° being more intense than the diffraction line at diffraction angle 2θ of 9.9±0.2°, and the diffraction line at diffraction angle 2θ of 9.9±0.2° being less than 0.4 times as intense as the diffraction line at diffraction angle 2θ of 9.3±0.2°.

2. The adduct according to claim 1, wherein $3.8<m \leq 4.2$ and $0<n \leq 0.7$.

3. The adduct according to claim 2, wherein the diffraction line at diffraction angle 2θ of 9.9±0.2° is less than 0.3 times as intense as the diffraction line at diffraction angle 2θ of 9.3±0.2°.

4. The adduct according to claim 1, further comprising a diffraction line at diffraction angle 2θ of 8.1±0.2°, the diffraction line at diffraction angle 2θ of 8.1±0.2° being less than 0.7 times as intense as the diffraction line at diffraction angle 2θ of 9.9±0.2°.

5. The adduct according to claim 1, wherein the adduct has only one melting peak between 90–105° C. in a DSC profile.

6. The adduct according to claim 5, wherein the melting peak has an associated fusion enthalpy lower than 125 J/g.

7. The adduct according to claim 6, wherein the associated fusion enthalpy is lower than 110 J/g.

8. The adduct according to claim 1, wherein the adduct is in spheroidal particle form.

9. A catalyst component for polymerizing olefins comprising a product of a reaction between a transition metal compound and a $MgCl_2 \cdot mEtOH \cdot nH_2O$ adduct, $3.4<m \leq 4.4$, $0<n \leq 0.7$, the adduct having an X-ray diffraction spectrum comprising at least one diffraction line at each diffraction angle 2θ of 9.3±0.2° and 9.9±0.2° with each diffraction angle being between 5° and 10°, the diffraction line at diffraction angle 2θ of 9.3±0.2° being more intense than the diffraction line at diffraction angle 2θ of 9.9±0.2° being less than 0.4 times as intense as the diffraction line at diffraction angle 2θ of 9.3±0.2°.

10. The catalyst component according to claim 9, wherein the transition metal compound is a titanium compound of formula $Ti(OR)_n X_{y-n}$ in which n is between 0 and y; y is a valence of titanium; X is a halogen and R is an alkyl radical having 1–8 carbon atoms or a COR' group wherein R' is an alkyl radical having 1–8 carbon atoms.

11. The catalyst component according to claim 10, wherein the titanium compound is selected from $TiCl_3$, $TiCl_4$, $Ti(OBu)_4$, $Ti(OBu)Cl_3$, $Ti(OBu)_2Cl_2$, and $Ti(OBu)_3Cl$.

12. The catalyst component according to claim 9, wherein the reaction between the transition metal compound and the adduct further comprises an electron donor compound.

13. The catalyst component according to claim 12, wherein the electron donor compound is selected from esters, ether, amines, and ketones.

14. The catalyst component according to claim 12, wherein the electron donor compound is selected from alkyl or aryl esters of mono or polycarboxylic acids.

15. The catalyst component according to claim 12, wherein the electron donor compound is selected from 1,3 diethers of formula:

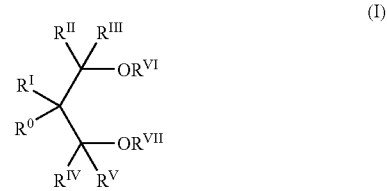

(I)

wherein $R^O$, $R^I$, $R^{II}$, $R^{III}$, $R^{IV}$ and $R^V$, are equal or different from each other, and are hydrogen or hydrocarbon radicals having from 1 to 18 carbon atoms, and $R^{VI}$ and $R^{VII}$, are equal or different from each other, and are hydrocarbon radicals having from 1 to 18 carbon atoms, optionally with one or more of R—R$^{VII}$ linked to form a cyclic group.

16. A catalyst component for polymerizing olefins comprising a product of a reaction between a transition metal compound and a partially dealcoholated MgCl$_2$-ethanol adduct obtained by partial dealcoholation of a MgCl$_2$·mEtOH·nH$_2$O adduct, wherein 3.4<m≦4.4, 0<n≦0.7, the MgCl$_2$·mEtOH·nH$_2$O adduct having an X-ray diffraction spectrum comprising at least one diffraction line at each diffraction angle 2θ of 9.3±0.2° and 9.9±0.2° with each diffraction angle being between 5° and 10°, the diffraction line at diffraction angle 2θ of 9.3±0.2° being more intense than the diffraction line at diffraction angle 2θ of 9.9±0.2°, and the diffraction line at diffraction angle 2θ of 9.9±0.2° being less than 0.4 times as intense as the diffraction line at diffraction angle 2θ of 9.3±0.2°.

17. The catalyst component according to claim 16, wherein the partially dealcoholated MgCl$_2$-ethanol adduct contains from 0.1 to 3 moles of ethanol per mole of MgCl$_2$.

18. The catalyst component according to claim 17, wherein the partially dealcoholated MgCl$_2$-ethanol adduct has a porosity ranging from 0.5 to 2 cc/g.

19. The catalyst component according to claim 17, wherein the partially dealcoholated MgCl$_2$-ethanol adduct contains from 1 to 3 moles of ethanol per mole of MgCl$_2$ and a porosity ranging from 0.15 to 1.5 cc/g.

20. A catalyst for polymerizing olefins comprising a product of a reaction between a catalyst component, which comprises a product of a reaction between a transition metal compound and a MgCl$_2$·mEtOH·nH$_2$O adduct wherein 3.4<m≦4.4, 0<n≦0.7, the adduct having an X-ray diffraction spectrum comprising at least one diffraction line at each diffraction angle 2θ of 9.3±0.2° and 9.9±0.2° with each diffraction angle being between 5° and 10°, the diffraction line at diffraction angle 2θ of 9.3±0.2° being more intense than the diffraction line at diffraction angle 2θ of 9.9±0.2°, and the diffraction line at diffraction angle 2θ of 9.9±0.2° being less than 0.4 times as intense as the diffraction line at diffraction angle 2θ of 9.3±0.2°.

21. The catalyst for polymerizing olefins according to claim 20, wherein the organoaluminum compound is an Al-trialkyl compound.

22. The catalyst for polymerizing olefins according to claim 21, further comprising an external donor.

23. The catalyst for polymerizing olefins according to claim 22, wherein the external donor is selected from silane compounds containing at least one Si—OR link, having a formula of R$_a^1$R$_b^2$Si(OR$^3$)$_c$, where a and b are integer from 0 to 2, c is an integer from 1 to 3, and the sum (a+b+c) is 4; R$^1$, R$^2$, and R$^3$, are alkyl, cycloalkyl, or aryl radicals with 1–18 carbon atoms.

24. A process for polymerizing olefins of formula CH$_2$=CHR$^4$, in which R$^4$ is hydrogen or a hydrocarbon radical having 1–12 carbon atoms, comprising a catalyst for polymerizing olefins comprising a product of a reaction between a catalyst component for polymerizing olefins comprising a product of a reaction between a transition metal compound and a MgCl$_2$·mEtOH·nH$_2$O adduct wherein 3.4<m≦4.4, 0<n≦0.7, the adduct having an X-ray diffraction spectrum comprising at least one diffraction line at each diffraction angle 2θ of 9.3±0.2° and 9.9±0.2° with each diffraction angle being between 5° and 10°, the diffraction line at diffraction angle 2θ of 9.3±0.2° being more intense than the diffraction line at diffraction angle 2θ of 9.9±0.2°, and the diffraction line at diffraction angle 2θ of 9.9±0.2° being less than 0.4 times as intense as the diffraction line at diffraction angle 2θ of 9.3±0.2°, and an organoaluminum compound.

25. A catalyst for polymerizing olefins comprising a product of a reaction between a catalyst component, which comprises a product of a reaction between a transition metal compound and a partially dealcoholated MgCl$_2$-ethanol adduct obtained by partial dealcoholation of a MgCl$_2$·mEtOH·nH$_2$O adduct wherein 3.4<m≦4.4, 0<n≦0.7, the adduct having an X-ray diffraction spectrum comprising at least one diffraction line at each diffraction angle 2θ of 9.3±0.2° and 9/9±0.2° with each diffraction angle being between 5° and 10°, the diffraction line at diffraction angle 2θ of 9.3±0.2° being more intense than the diffraction line at diffraction angle 2θ of 9.9±0.2°, and the diffraction line at diffraction angle 2θ of 9.9±0.2° being less than 0.4 times as intense as the diffraction line at diffraction angle 2θ of 9.3±0.2°, and an organoaluminum compound.

26. A process for polymerizing olefins of formula CH$_2$=CHR$^4$, wherein R$^4$ is hydrogen or a hydrocarbon radical having 1–12 carbon atoms, comprising a catalyst for polymerizing olefins comprising a product of a reaction between a transition metal compound and a partially dealcoholated MgCl$_2$-ethanol adduct obtained by partial dealcoholation of a MgCl$_2$·mEtOH·nH$_2$O adduct wherein 3.4<m≦4.4, 0<n≦0.7, the adduct having an X-ray diffraction spectrum comprising at least one diffraction line at each diffraction angle 2θ of 9.3±0.2° and 9.9±0.2° with each diffraction angle being between 5° and 10°, the diffraction line at diffraction angle 2θ of 9.3±0.2° being more intense than the diffraction line at diffraction angle 2θ of 9.9±0.2°, and the diffraction line at diffraction angle 2θ of 9.9±0.2° being less than 0.4 times as intense as the diffraction line at diffraction angle 2θ of 9.3±0.2°, and an organoaluminum compound.

* * * * *

UNITED STATES PATENT AND TRADEMARK OFFICE
CERTIFICATE OF CORRECTION

PATENT NO. : 7,087,688 B2
APPLICATION NO. : 10/495940
DATED : August 8, 2006
INVENTOR(S) : Daniele Evangelisti et al.

It is certified that error appears in the above-identified patent and that said Letters Patent is hereby corrected as shown below:

At col. 10, line 30, claim 35, line 10, before "being" insert --, and the diffraction line at diffraction angle 2θ of 9.9 ± 0.2°--

At col. 10, line 47, claim 39, line 3, change "ether" to --ethers--

At col. 11, line 23, claim 44, line 3, change "0.5" to --0.05--

Signed and Sealed this

Second Day of September, 2008

JON W. DUDAS
*Director of the United States Patent and Trademark Office*